(12) United States Patent
Park et al.

(10) Patent No.: US 9,417,202 B2
(45) Date of Patent: Aug. 16, 2016

(54) SENSOR

(71) Applicant: INNOCHIPS TECHNOLOGY CO., LTD., Ansan-Si, Gyeonggi-Do (KR)

(72) Inventors: In Kil Park, Seongnam-Si (KR); Tae Hyung Noh, Siheung-Si (KR); Sung Cheol Park, Ansan-Si (KR); Ki Beom Kwon, Ansan-Si (KR); Seung Hwan Lee, Siheung-Si (KR); Jun Ho Jung, Siheung-Si (KR)

(73) Assignee: INNOCHIPS TECHNOLOGY CO., LTD. (KR)

( * ) Notice: Subject to any disclaimer, the term of this patent is extended or adjusted under 35 U.S.C. 154(b) by 0 days.

(21) Appl. No.: 14/678,981

(22) Filed: Apr. 4, 2015

(65) Prior Publication Data

US 2015/0285754 A1 Oct. 8, 2015

(30) Foreign Application Priority Data

Apr. 7, 2014 (KR) .......................... 10-2014-0041128

(51) Int. Cl.
  *H01L 27/14* (2006.01)
  *G01N 27/12* (2006.01)

(52) U.S. Cl.
  CPC ...................................... *G01N 27/12* (2013.01)

(58) Field of Classification Search
  CPC .................................................... G01N 27/12
  USPC .......................................................... 257/414
  See application file for complete search history.

(56) References Cited

U.S. PATENT DOCUMENTS

| 4,935,289 A | 6/1990 | Kikuchi et al. |
| 2005/0199041 A1 | 9/2005 | Weber et al. |
| 2010/0147070 A1* | 6/2010 | Jun ................... G01N 27/121 73/335.05 |
| 2014/0042025 A1* | 2/2014 | Furuta ................ G01N 27/4076 204/427 |

FOREIGN PATENT DOCUMENTS

| EP | 0798554 B1 | 10/1997 |
| JP | 57178146 | 11/1982 |
| JP | 61139762 | 6/1986 |
| JP | 335153 | 2/1991 |
| JP | 2006194853 | 7/2006 |
| JP | 2010112740 | 5/2010 |
| JP | 201268069 | 4/2012 |
| KR | 19970028533 B1 | 6/1997 |
| KR | 20040016605 A | 2/2004 |
| KR | 100618627 B1 | 9/2006 |
| KR | 100809421 B1 | 3/2008 |
| KR | 100843169 | 7/2008 |
| TW | 201239325 | 10/2012 |

* cited by examiner

*Primary Examiner* — Anthony Ho (57) ABSTRACT

Provided is a sensor including an insulating layer, at least two heater patterns separated in one direction in the insulating layer and electrically connected to each other, at least two sensing electrode patterns insulated form the heater patterns, separated in the one direction in the insulating layer, and electrically connected to each other, and a sensing material, at least a part of which is buried in the insulating layer to contact the sensing electrode patterns.

21 Claims, 8 Drawing Sheets

FIG. 9

SENSOR

CROSS-REFERENCE TO RELATED APPLICATION

This application claims priority to Korean Patent Application No. 10-2014-0041128 filed on Apr. 7, 2014 and all the benefits accruing therefrom under 35 U.S.C. §119, the contents of which are incorporated by reference in their entirety.

BACKGROUND

The present disclosure relates to a senor, and more particularly, to a sensor capable of improving shock-proof and sensitivity.

As an interest in recent living environmental pollution and health increases, necessity for sensing various environmental toxic gases is greatly increased. Toxic gas sensors having been developed by demands on sensing toxic gases and exploded gases are in a high demand due to needs for health care, living environment monitoring, industrial safety, home appliances and smart home, and improvement of the quality of human life for national defense and terrorism. Accordingly, a gas sensor becomes a means for realizing a society without a disaster and to this end, more precise measurement and controls for the environmental toxic gas are required than before.

Gas sensors may be classified into a semiconductor type gas sensor, a solid electrolyte gas sensor, and a catalytic combustion gas sensor according to a form, structure and material. The semiconductor type gas sensor among them has a large output change at a low concentration to have high sensitivity and be durable. Since operating at about 100° C. to 500° C., the semiconductor type gas sensor includes a sensing electrode for sensing a resistance change, a sensing material coated on the sensing electrode, and a heater (heating element) for raising a temperature of the sensing material. When the semiconductor type gas sensor is heated by a heater and a gas is adsorbed to the sensing material, the semiconductor type gas sensor measures an electrical characteristic change occurring between the sensing electrode and the sensing material by the adsorbed gas.

However, the semiconductor gas sensor does not normally operate, when adhesion between a sensing material and a sensing electrode is unstable or poor. In other words, since the semiconductor gas sensor has a structure that a sensing electrode is formed on a flat substrate and a sensing material is coated thereon, adhesion between the sensing electrode and the sensing material is very weak to an external shock. In addition, when, for example, a metal oxide semiconductor is used as a sensing material, an operation temperature of the semiconductor gas sensor is relative high as 250° C.~400° C., a phenomenon that the sensing material is desorbed due to a heat shock according to repetitive operations.

In addition, in typical gas sensors, a sensing electrode and an external electrode for PCB mount is connected by using wire bonding. An example of such a gas sensor is disclosed in Korean Patent Application Laid open Publication No. 2004-016605. However, the wire bonding is weak to an external shock and has difficulty in mass production.

SUMMARY

The present disclosure provides a sensor capable of improving shock-proof and accordingly preventing desorption of the electrode and sensing material.

The present disclosure also provides a sensor capable of improving response and sensitivity and enabling mass production.

The present disclosure also provides a sensor capable of improving a heat loss of a heater to enhance heat efficiency.

In accordance with an exemplary embodiment, a sensor includes: an insulating layer; at least two heater patterns separated in one direction in the insulating layer and electrically connected to each other; at least two sensing electrode patterns insulated form the heater patterns, separated in the one direction in the insulating layer, and electrically connected to each other; and a sensing material, at least a part of which is buried in the insulating layer to contact the sensing electrode patterns.

The insulating layer may include a plurality of stacked ceramic plates.

The sensor may further include first and second exposed electrodes formed to be exposed externally at predetermined areas in the insulating layer and configured to supply power to each of the heaters and the sensing electrodes.

The at least two heater patterns may be respectively formed on top portions of at least two ceramic plates and connected through a hole with a conductive material buried therein.

The at least two sensing electrode patterns may be respectively formed on at least two ceramic plates and connected through a hole with a conductive material buried therein.

The at least two sensing electrode patterns may include a (+) power applied sensing electrode pattern and a (−) power applied sensing electrode pattern separated from each other.

The sensing electrode patterns may include at least one cut-out portion.

The heat patterns and the sensing electrode patterns may be formed on different ceramic plates to be alternately disposed in a stack direction of the ceramic plates.

The sensing electrode patterns may be formed to have diameters being wider progressively from a bottom side toward a top side.

Openings may be formed inside the heater patterns and sensing electrode patterns in the at least two ceramic plates and buried with the conductive material.

The openings may be formed to expose the sensing electrode patterns thereunder.

The sensor may further include a top cover disposed on a top portion of the insulating layer to cover the sensing material, wherein the top cover is formed of at least two stacked ceramic plates, or a metal or plastic, and includes at least one opening or a mesh.

The opening of the top cover may be greater than that of the insulating layer.

The sensor may further include a heat sink disposed on a bottom portion of the insulating layer, wherein the heat sink is formed of at least two stacked ceramic plates, and the at least one ceramic plate includes an opening.

The sensor may further include a third exposed electrode formed on a predetermined area of the heat sink, which corresponds to the first and second exposed electrodes.

The sensor may further include a bottom cover disposed on a bottom portion of the heat sink.

In accordance with another exemplary embodiment, a sensor includes: a plurality of unit sensors each including heaters, sensing electrodes, and a sensing material formed in a vertical direction in an insulating layer to sense at least one gas, wherein the heaters, the sensing electrodes, and the sensing material are disposed in plurality in a horizontal direction and sense a plurality of different subjects, wherein the heaters are separated in the vertical direction in the insulating layer and electrically connected to each other, the sensing electrodes are insulated from the heaters and vertically separated in the insulating layer to be electrically connected to each other, and the sensing material, at least a part of which is buried in the insulating layer to contact the sensing electrodes.

The plurality of heaters arranged in the horizontal direction may heat at at least two temperatures.

The plurality of sensing electrodes may respectively include at least one cut-out portion.

The plurality of sensing materials may be formed of at least two materials.

The sensor may further include: a top cover disposed on a top portion of the insulating layer to cover the sensing material, a heat sink disposed on a bottom portion of the insulating layer; and a bottom cover disposed on a bottom portion of the heat sink.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Hereinafter, specific embodiments will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Figure 1:
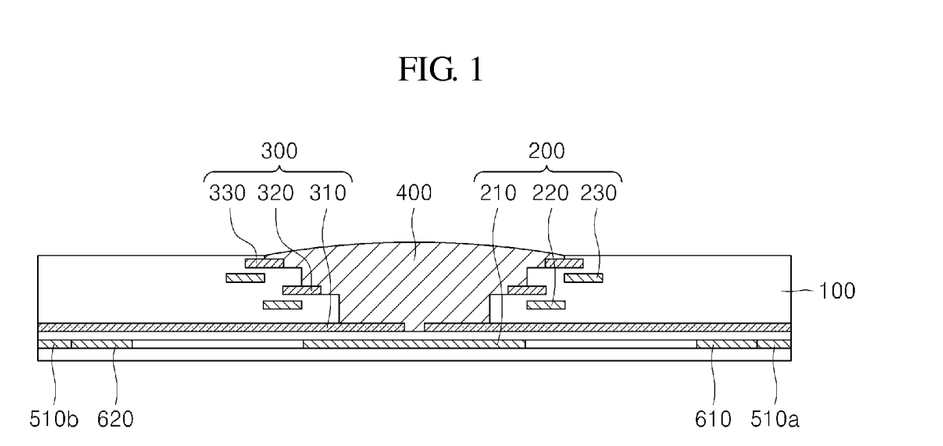
FIGS. 1 and 2 are a combined cross-sectional view and an exploded perspective view of a gas sensor in accordance with an exemplary embodiment.
Figure 2:
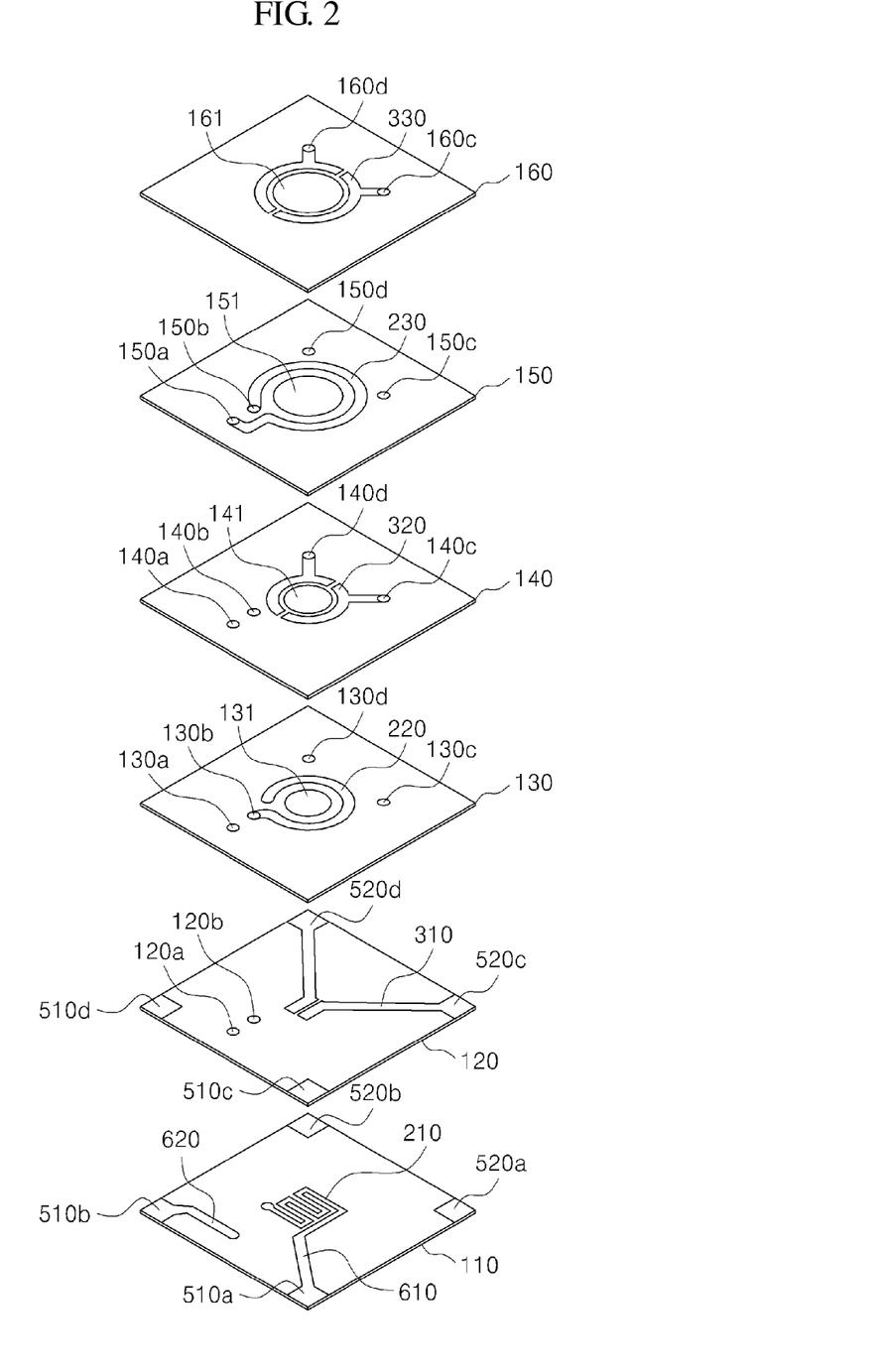

FIG. 1 is a combined cross-sectional view of a gas sensor in accordance with an exemplary embodiment, and FIG. 2 is an exploded perspective view.

Referring to FIGS. 1 and 2, a gas sensor in accordance of an exemplary embodiment may include a plurality of insulting layers 100 (100 to 160) stacked in a vertical direction, a heater 200 including heater patterns 210, 220, and 230 formed on at least two selected insulating layers 100, a sensing electrode 300 including sensing electrode patterns 310, 320, and 330 formed on at least two selected insulating layers 100 on which the heat pattern 210, 220, and 230 are not formed, and a sensing material 400 disposed in at least one insulating layer 100 and contacting the sensing electrode 300. In other words, in the gas sensor of the embodiment, the heat patterns 210, 220, and 230 are vertically separated to be formed in the plurality of insulating layers 100, the sensing electrode patterns 310, 320, and 330 are vertically separated to be formed in the insulating layers 100 in which the heater patterns 210, 220, and 230 are not formed, and the sensing material 400 is buried in openings 131, 141, 151, and 161 formed in predetermined areas of the plurality of insulating layers 100 to contact the sensing electrode patterns 310, 320, and 330. Accordingly, the gas sensor of the embodiment has a 3-dimensional structure in which the plurality of heater patterns 210, 220, and 230 and sensing electrode patterns 310, 320, and 330 are vertically formed and the sensing material 400 is buried inside a predetermined insulating layer 100. In addition, the heater 200 may have one heater pattern, not in plurality. In other words, the heater 200 may include only the heat pattern 210. Furthermore, the gas sensor of an embodiment further includes first and second exposed electrodes 510 and 520 exposed externally at predetermined areas of at least two insulating layers 100 for supplying power to each of the heater 200 and the sensing electrode 300 from the outside, and interconnections 600 for connecting the first exposed electrode 510 and the heater 200.

The plurality of insulating layers 100 (110 to 160) may use, for example, ceramic plates having a predetermined thickness. To this end, for example, a raw material powder is disposed by mixing $B_2O_3$—$SiO_2$-based glass, $Al_2O_3$—$SiO_2$-based glass, and other ceramic materials with a composition including $Al_2O_3$, and glass frit, etc., and ball-milling the mixed result with a solvent such as alcohol, the raw material powder and an organic binder is melted in toluene/alcohol-based solvent as an additive to be input thereto, a slurry is manufactured by milling a result with a small ball mill and mixing, and then a plate having a desired thickness may be manufactured by a doctor blade method with the slurry. The openings 131, 141, 151, and 161 of a predetermined size may be formed, for example, at central portions of at least two of the plurality of insulating layers 100. In addition, at least two holes may be formed in the at least two insulating layers 100 other than the openings 131, 141, 151, and 161. The openings 131, 141, 151, and 161 are filled with the sensing material 400 and at least two holes are filled with a conductive material.

The heater 200 plays a role for maintaining a temperature of the sensing material 400 in order for the sensor not to be affected by an external temperature. The heater 200 may include a plurality of heater patterns 210, 220, and 230 vertically separated and electrically connected to each other. For example, the heater 200 may include first to third heater patterns 210, 220, and 230 respectively formed on the first, third, and fifth insulating layers 110, 130 and 150. In addition, the first to third heater patterns 210, 220, and 230 may be connected through first holes 120a, 130a, 140a, 150a and second holes 120b, 130b, 140b, 150b formed in predetermined areas of the second, third, and fourth insulating layers 120, 130, and 140. In other words, the heater 200 of the embodiment may be vertically formed in plurality from a plane, namely, a top surface of the insulated layer 100 and electrically connected to each other. In addition, the heater 200 including the first to third heater patterns 210, 220, and 230 may be connected to the first exposed electrode 510 through a heater interconnection 610 formed to be connected to the first heater pattern 210 on the first insulating layer 110. Furthermore, the heater 200 may be formed of a conductive material, for example, a metal material including gold (Au), platinum (Pt), aluminum (Al), molybdenum (Mo), silver (Ag), TiN, tungsten (W), ruthenium (Ru), or iridium (Ir), or a mixture of metal materials. In addition, the heater 200 and the sensing electrode 300 may be implemented as a double layer by using a material for increasing adhesion of a metal material such as chromium (Cr) or Titanium (Ti), and a metal material.

The sensing electrode 300 plays a role for contacting the sensing material 400 to sense an electrical characteristic change of the sensing material 400. The sensing electrode 300 may include a plurality of sensing electrode patterns 310, 320, and 330 vertically separated and electrically connected to each other. For example, the sensing electrode 300 may include first, second, and third sensing electrode pattern 310, 320, and 330 respectively formed on insulating layers on which the heater patterns 210, 220, and 230 are not formed, namely, the second, fourth, and sixth insulating layers 120, 140, and 160. In addition, the first to third sensing electrode patterns 310, 320, and 330 may be connected through third holes 130c, 140c, 150c, and 160c and fourth holes 130d, 140d, 150d, and 160d formed on each of the third, fourth and fifth insulating layers 130, 140, and 150. The third holes 130c, 140c, 150c, 160c and the fourth holes 130d, 140d, 150d, 160d are separated from each other, and also separated from the first holes 120a, 130a, 140a, and 150a, and the second holes 120b, 130b, 140b, and 150b. In other words, the sensing electrode 300 of the embodiment may be vertically formed in plurality from a plane, namely, a top surface of the insulating layer 100, on a different insulating layer 100 from the heater 200. In addition, in the sensing electrode 300, the first sensing electrode pattern 310 is extended to be connected to the second exposed electrode 520. The sensing electrode 300 may be formed of a conductive material, for example, a metal material including gold (Au), platinum (Pt), aluminum (Al), molybdenum (Mo), silver (Ag), TiN, tungsten (W), ruthenium (Ru), or iridium (Ir), or a mixture of metal materials. In addition, the heater 200 and the sensing electrode 300 may be implemented as a double layer by using a material for increasing adhesion of a metal material such as chromium (Cr) or Titanium (Ti), and a metal material.

The sensing material 400 uses a material of which an electrical characteristic is changed according to an amount of a material desired to sense. The sensing material 400 may include a mixture material of an insulator and a conductor. For example, the sensing materials 400 may include a material that a catalyst such as Pt, Pd, Ag, or Ni is mixed to any one parent material selected from among SnO2, ZnO, $Fe_2O_3$, $WO_3$, and $TiO_2$. Here, the sensing material 400 may be buried in predetermined areas of the third, fourth, fifth, and sixth insulating layers 130, 140, 150, and 160, for example, openings 131, 141, 151, and 161 formed at central portions of the third, fourth, fifth and sixth insulating layers 130, 140, 150, and 160. At this point, the sensing material 400 are formed to contact the first to third sensing electrode patterns 310, 320, and 330 exposed by the openings 131, 141, 151, and 161.

The gas sensor according to an embodiment will be described in detail with reference to an exploded perspective view of FIG. 2.

The first insulating layer 110 includes thereon the first heater pattern 210, the first exposed electrodes 510 (510a and 510b) for supplying external power to the heater 200 including the first heater pattern 210, the second exposed electrodes 520 (520a and 520b) for supplying the external power to the sensing electrode 300, and the interconnections 600 (610 and 620) connecting the heater 200 including the first heater pattern 210 and the first exposed electrodes 510. The first heater pattern 210 may be formed by using a conductive material at, for example, the central portion of the first insulating layer 110. In addition, the first heater pattern 210 may be in a spiral form having a predetermined width and interval, and the width and interval of the first heater pattern 210 may be uniform. The first exposed electrodes 510 (510a and 510b) are formed to be exposed externally at predetermined areas including first and second corners adjacent to each other in one direction of the quadrangular first insulating layer 110. In addition, the second exposed electrodes 520 (520a and 520b) are formed to be exposed externally at predetermined areas including third and fourth corners of the first insulating layer 110 on which the first exposed electrodes 510 are not formed. In other words, the first exposed electrodes 510 are respectively formed at the predetermined areas including the first and second corners adjacent to each other in one direction of the first insulating layers 110, and the second exposed electrodes 520 are respectively formed at the predetermined areas including the third and fourth corners adjacent to the first and second corners in the other direction at which the first exposed electrodes 510 are formed. The first interconnection 610 is connected to one end of the first heater pattern 210 to be extended, for example, in a diagonal direction of the first insulating layer 110 and connected to the first exposed electrode 510a. The first interconnections 610 may be formed in various forms such as an "L" shape or an inversed "L" shape. In addition, the second interconnections 620 are formed separately from the first heat pattern 210 and extended in one direction from the first exposed electrode 510b.

The second insulating layer 120 includes thereon the first sensing electrode pattern 310, the first exposed electrodes 510 (510c and 510d) for supplying power to the heater 200 from the outside, the second exposed electrodes 520 (520c, 520d) connected to the first sensing electrode pattern 310 and supplying power to the sensing electrodes 300 from the outside, and first and second holes 120a and 120b connected to the heater 200 and having a conductive material buried therein. The first sensing electrode pattern 310 is formed on a predetermined area of the second insulating layer 120 to overlap at least a part of the first heat pattern 210 formed on the first insulating layer 110. For example, the first sensing electrode pattern 310 is formed on the central portion of the second insulating layer 120. In addition, the first sensing electrode pattern 310 is formed so that two electrodes having a predetermined width are separated from each other on the central portion of the second insulating layer 120. In addition, the two electrodes separated from each other by a predetermined interval are extended in a diagonal direction of the second insulating layer 120 to be respectively connected to the second exposed electrodes 520. In other words, the first sensing electrode pattern 310 is formed to be separated from the central portion of the second insulating layer 120 with the predetermined width by the predetermined interval and extended therefrom in the diagonal direction. In addition, the second exposed electrodes 520 formed on the second insulating layer 120 are formed on identical areas to the second exposed electrodes formed on the first insulating layer 110. Accordingly, the second exposed electrodes 520 respectively formed on the first and second insulating layers 120 are formed to be overlapped. In other words, the first exposed electrodes 510 are formed on two corner portions of the second insulating layer 120 at which the second exposed electrodes 520 are not formed. The first exposed electrodes 510 formed on the second insulating layer 120 are formed to overlap the first exposed electrodes 510 formed on the first insulating layer 110. In addition, the first hole 120a is formed in an area corresponding to an area of the first heater pattern 210 formed on the first insulating layer 110. For example, the second hole 120b is formed in an area corresponding to another end of the first heater pattern 210, namely, the other end of the first heat pattern 210 separated from one end thereof connected to the second interconnection 620. In addition, the first hole 120a is formed in an area corresponding to one end of the second interconnection 620 formed on the first insulating layer 110. In other words, the one end of the second interconnection 620 is connected to the first exposed electrodes 510 and the first hole 120a is formed in an area corresponding to the other end thereof.

An opening 131 is formed in the central portion of the third insulating layer 130, and the second heater pattern 220 is formed around the opening 131 to surround the opening 131. The opening 131 is formed in, for example, the central portion of the third insulating layer 130 in, for example, a circular form and filled with the sensing material 400. In addition, the second heater pattern 220 is formed to be separated from the opening 131 by a predetermined interval and to surround the opening 131 in, for example, a circular form. At this point, the second heater pattern 220 may be formed so that one end and the other end thereof are separated from each other by a predetermined interval. The opening 131 may be formed in various forms such as a quadrangle, triangle, and ellipse, and the second heater pattern 220 may be formed to be separated from the opening 131 by a predetermined interval in various forms including the form of the opening 131. In addition, the first and second holes 130a and 130b are respectively formed in predetermined areas of the third insulating layer 130 corresponding to the first and second holes 120a and 120b formed on the second insulating layer 120. Here, the one end of the second heater pattern 220 may be extended to the second hole 130b. In other words, third and fourth holes 130c and 130d may be formed in predetermined areas of the third insulating layer 130. The third and fourth holes 130c and 130d may be formed to expose a predetermined area of the first sensing electrode pattern 310 extended to the second exposed electrodes 520 formed on the second insulating layer 120.

An opening 141 is formed in the central portion of the fourth insulating layer 140, and the second sensing electrode pattern 320 is formed around the opening 141 to surround the opening 141. The opening 141 is formed in, for example, the central portion of the fourth insulating layer 140, for example, in a circular form and filled with the sensing material 400. In addition, the opening 141 may be formed to have an identical size and form to those of the opening 131 formed on the third insulating layer 130. However, the opening 141 may be formed differently from the opening 131 and also formed smaller or greater than the opening 131. The second heater pattern 320 is formed to be separated from the opening 141 by a predetermined interval and to surround the opening 141 in, for example, a circular form. At this point, the second sensing electrode pattern 320 is formed so that one end and the other end thereof contact. The opening 141 may be formed in various forms such as a quadrangle, triangle, and ellipse, and the second heater pattern 320 may be formed to be separated from the opening 141 by a predetermined interval in various forms including the form of the opening 141. In addition, first and second holes 140a and 140b are respectively formed in predetermined areas of the fourth insulating layer 140 corresponding to the first and second holes 130a and 130b formed in the third insulating layer 130. Furthermore, third and fourth holes 140c and 140d are formed in predetermined areas of the fourth insulating layer 140. The third and fourth holes 140a and 140d may be formed in identical areas to the third and fourth holes 130a and 130d formed in the third insulating layer 130. In addition, the second sensing electrode pattern 320 may be extended to the third and fourth holes 130c and 130d from predetermined areas. In other words, the second sensing electrode pattern 320 is formed in an approximately circular form and may further include an extended area extended to the third and fourth holes 130c and 130d from the predetermined areas.

An opening 151 is formed in the central portion of the fifth insulating layer 150, and the third heater pattern 230 is formed around the opening 151 to surround the opening 151. The opening 151 is formed in, for example, the central portion of the fifth insulating layer 150, for example, in a circular form and filled with the sensing material 400. In addition, the third heater pattern 230 is formed to be separated from the opening 151 by a predetermined interval and to surround the opening 151 in, for example, a circular form. At this point, the third heater pattern 230 may be formed so that one end and the other end thereof are separated from each other by a predetermined interval. The opening 151 may be formed in various forms such as a quadrangle, triangle, and ellipse, and the third heater pattern 230 may be formed to be separated from the opening 151 by a predetermined interval in various forms including the form of the opening 151. In addition, the opening 151 may be formed greater than the openings 131 and 141 respectively formed in the third and fourth insulating layers 130 and 140. In other words, the opening 151 may be formed so that at least a part of the second sensing electrode pattern 320 formed on the fourth insulating layer 140 is exposed. In other words, the first and second holes 150a and 150b are respectively formed in predetermined areas of the fifth insulating layer 150, which correspond to the first holes 120a, 130a, and 140a and the second holes 120b, 130b, and 140b respectively formed in the second, third, and fourth insulating layers 120, 130, and 140. In addition, one end of the third heater pattern 230 may be extended to the first hole 150a and the other end thereof may be extended to the second hole 150b. Furthermore, third and fourth holes 150c and 150d may be formed in predetermined areas of the fifth insulating layer 150. The third and fourth holes 150c and 150d are formed in areas corresponding to the third holes 130a and 140a and the fourth holes 130b and 140b formed in the third and fourth insulating layers 130 and 140.

An opening 161 is formed in the central portion of the sixth insulating layer 160, and the third sensing electrode pattern 330 is formed around the opening 161 to surround the opening 161. The opening 161 is formed in, for example, the central portion of the sixth insulating layer 160, for example, in a circular form and filled with the sensing material 400. In addition, the opening 161 may be formed to have an identical size and form to those of the opening 151 formed on the third insulating layer 150. However, the opening 161 may be formed differently from the opening 151 and also formed smaller or greater than the opening 151. However, the opening 151 is formed in a size not to expose the third heat pattern 230 of the fifth insulating layer 150. The third sensing electrode pattern 330 is formed to be separated from the opening 161 by a predetermined interval and to surround the opening 141 in, for example, a circular form. At this point, the third sensing electrode pattern 330 is formed so that one end and the other end thereof contact. The opening 161 may be formed in various forms such as a quadrangle, triangle, and ellipse and the third sensing electrode pattern 330 may be formed to be separated from the opening 161 by a predetermined interval in various forms including the form of the opening 161. In addition, the third and fourth holes 160c and 160d may be formed in predetermined areas of the insulating layer 160. The third and fourth holes 160c and 160d may be formed in identical areas to the third and fourth holes 150c and 150d formed in the fifth insulating layer 150. In addition, the third sensing electrode pattern 330 may be extended to the third and fourth holes 160c and 160d from a predetermined area. In other words, the third sensing electrode pattern 330 may further include an extended area extended to the third and fourth holes 160c and 160d from the predetermined area.

As described above, in a gas sensor according to an embodiment, the plurality of ceramic insulating layers 110 to 160 are stacked, the heater 200 that the plurality of heater patterns 210, 220, and 230 are electrically connected in a vertical direction in the insulating layers 100, and a sensing electrode 300 is formed that a plurality of sensing electrode patterns 310, 320, and 330 are insulated from the heater patterns 210, 220, and 230 vertically in the insulating layers 100 and the plurality of sensing electrode patterns 310, 320, and 330 are electrically connected. In other words, the plurality of heater patterns 210, 220, and 230 and the sensing electrode patterns 310, 320, 330 are formed to be insulated in the plurality of stacked insulating layers 100, and the heater patterns 210, 220, and 230 are disposed on the bottom portion of the sensing electrode patterns 310, 320, and 330. In addition, the openings 131, 141, 151, and 161 are formed to respectively expose the sensing electrode patterns 310, 320, and 330 on predetermined areas of the plurality of insulating layers 100, and are buried with the sensing material 400. Accordingly, the heaters 200 and the sensing electrodes 300 are formed in a vertical direction and a gas sensor in a 3-dimensional structure having the sensing material 400 buried therein is implemented.

In an embodiment, since the sensing material 400 is buried in the plurality of stacked insulating layers 100, the sensing material is not desorbed. In addition, since the sensing material 400 contacts the plurality of sensing electrode patterns 310, 320, and 330, the adhesion may be improved by increasing a contact area of the sensing electrode 300 and the sensing material 400, and response and sensitivity may be improved. In addition, the gas sensor may be mounted by using a surface mount without wire-bonding by forming an exposed electrode to be exposed to a plurality of flat insulating layers 110 and 160 and soldering the exposed electrode.

Figure 3:
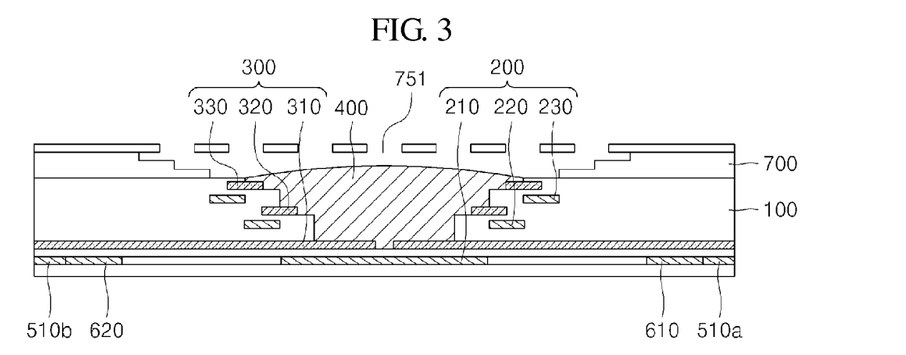
FIGS. 3 and 4 are a combined cross-sectional view and an exploded perspective view of a gas sensor in accordance with another exemplary embodiment.
Figure 4:
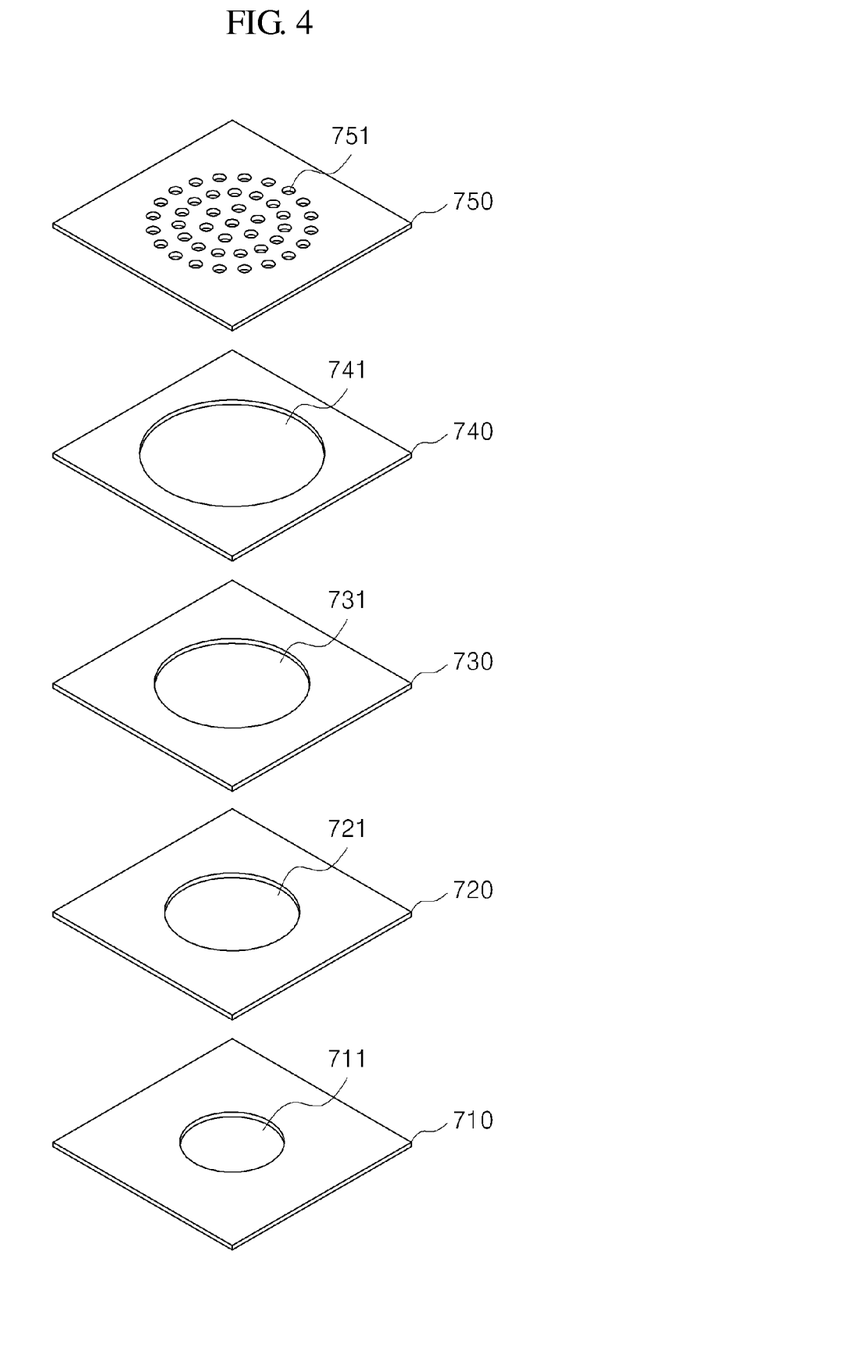

FIG. 3 is a combined cross-sectional view of a gas sensor in accordance with an exemplary embodiment, and FIG. 4 is an exploded perspective view.

Referring FIGS. 3 and 4, a gas sensor according to an embodiment further includes the top cover 700. In other words, the plurality of insulating layers 100 (110 to 160), the heaters 200 formed on at least two selected insulating layers 100, the sensing electrodes 300 formed in at least two selected insulating layers 100 on which the heaters 200 are not formed, the sensing material 400 disposed in at least one insulating layer 100 to contact the sensing electrodes 300, and a top cover 700 formed on the insulating layer 160 to cover the sensing material 400.

The top cover 700 may be disposed in order for the sensing material 400 not to be exposed externally. The top cover 700 may be formed by using a plurality of plates 710 to 750 having a predetermined thickness. The plurality of plates 710 to 750 may be manufactured with an identical material and in an identical thickness to those of the plurality of insulating layers 110 to 160. However, the plurality of plates 710 to 750 may be manufactured to be thinner or thicker than the plurality of insulating layers 110 to 160. The top cover 700 may be manufactured by using a metal or plastic, and boned to the substrates 100. In addition, a plurality of openings 711, 721, 731, and 741 are formed in, for example, the central portions in at least two selected plates, for example, the first to fourth plates 710 to 740. The openings 711, 721, 731, and 741 may be formed in different sizes, and formed greater progressively from the bottom side opening 711 toward the top side opening 741. At this point, the bottom side opening 711 may be greater than the opening 161 formed in the uppermost insulating layer 160. In other words, the openings 711, 721, 731, and 741 may be greater than, for example, an exposed area of the sensing material 400. The openings 711, 721, 731, and 741 may be formed in an identical size and form. In addition, a mesh may be formed in the uppermost plate 750. The mesh 751 may be formed in a small size not to allow a foreign material to penetrate therethrough, even though a gas moves through the mesh 751. At this point, the diameter of the area in which the mesh 751 is formed may be smaller than or equal to that of the opening 741 formed thereunder. Like this, by forming the openings 711, 721, 731, and 741 in the plurality of plates 710 to 740, a predetermined space is disposed in the top cover 700 and accordingly a time that a gas flowed into the top cover 700 through the mesh 751 contacts the sensing material 400 becomes longer, thereby improving response and sensitivity.

Figure 5:
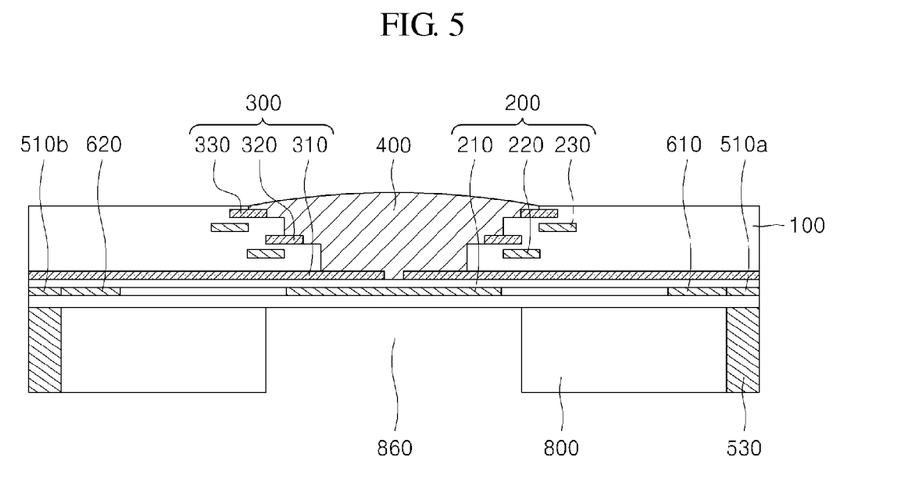
FIGS. 5 and 6 are a combined cross-sectional view and an exploded perspective view of a gas sensor in accordance with still another exemplary embodiment.
Figure 6:
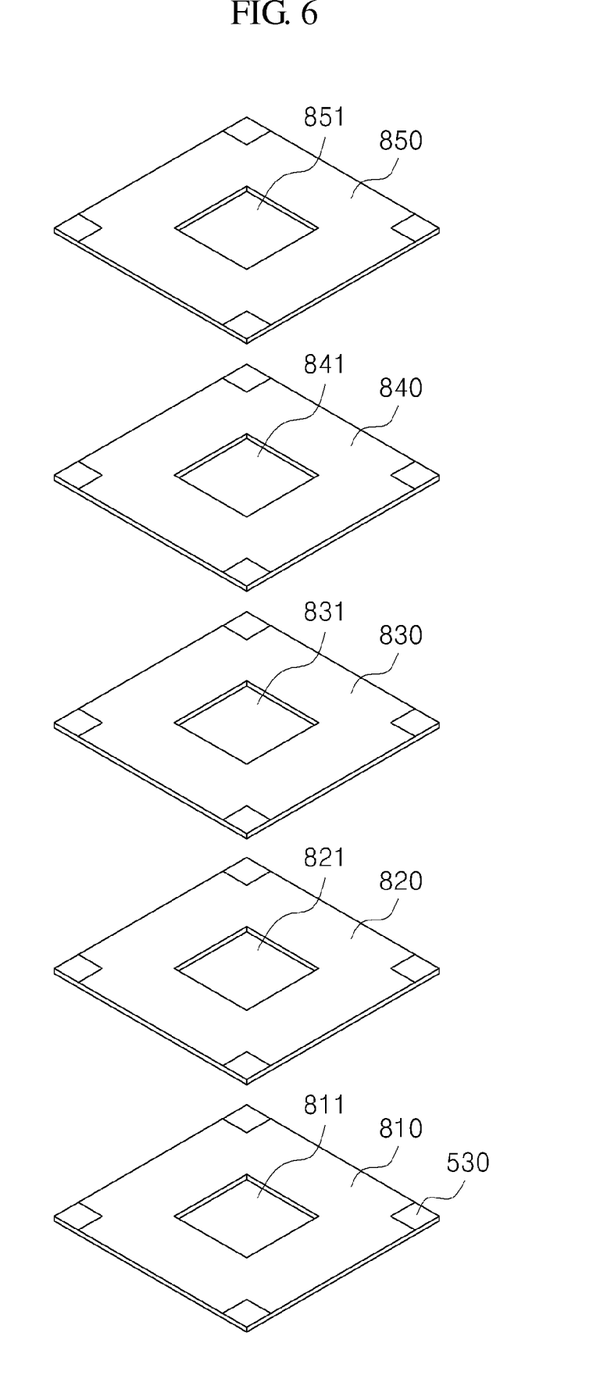

FIG. 5 is a combined cross-sectional view of a gas sensor in accordance with an exemplary embodiment, and FIG. 6 is a partial exploded perspective view.

Referring to FIGS. 5 and 6, a gas sensor according to an embodiment further includes a heat sink 800. In other words, the gas sensor includes the plurality of insulating layers 100 (110 to 160), the heaters 200 formed on at least two selected insulating layers 100, the sensing electrodes 300 formed on at least two selected insulating layers 100 on which the heaters 200 are not formed, the sensing material 400 disposed in at least one insulating layer 100 to contact the sensing electrodes 300, and a heat sink 800 formed on the bottom portion of the insulating layer 110.

The heat sink 600 may be disposed at the bottom portion of the insulating layer 110 to release heat generated by the heaters 200. The heat sink 800 may be formed by using a plurality of plates 810 to 850 having a predetermined thickness. The plurality of plates 810 to 850 may be manufactured with an identical material and in an identical thickness to those of the plurality of insulating layers 110 to 160. However, the plurality of plates 810 to 850 may be manufactured to be thinner or thicker than the plurality of insulating layers 110 to 160. In addition, openings 860 (811, 821, 831, 841, and 851) are formed, for example, in the central portions of the plurality of plates 810 to 850. The openings (811, 821, 831, 841, and 851) may be formed in an identical size and form, and formed greater than, for example, the first heater pattern 210. In addition, external electrode patterns 530 may be respectively formed at corners of the plurality of plates 810 to 850. The external electrode patterns 530 may be formed to be exposed externally to be soldered with the first and second exposed electrodes 510 and 520.

Figure 7:
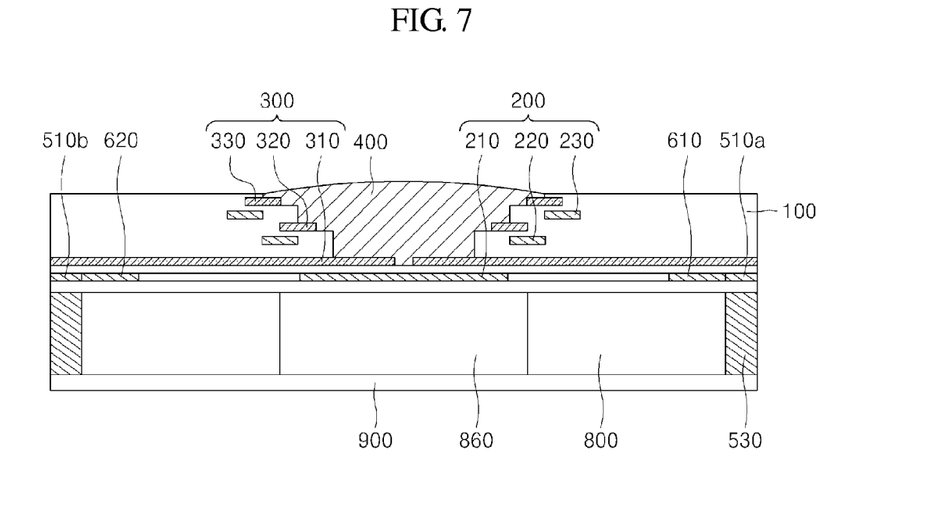
FIG. 7 is a combined cross-sectional view of a gas sensor in accordance with still another exemplary embodiment.

FIG. 7 is a combined cross-sectional view of a gas sensor in accordance with an exemplary embodiment.

Referring to FIG. 7, a gas sensor according an embodiment further includes a heat sink 800 and a bottom cover 900. In other words, the gas sensor includes the plurality of insulating layers 100 (110 to 160), the heaters 200 formed on at least two selected insulating layers 100, the sensing electrodes 300 formed on at least two selected insulating layers 100 on which the heaters 200 are not formed, the sensing material 400 disposed in at least one insulating layer 100 to contact the sensing electrode 300, the heat sink 800 disposed in the bottom portion of the insulating layer 110 to release heat generated by the heaters 200, and the bottom cover 900 disposed on the bottom surface of the heat sink 800 to cover an opening 860 of the heat sink 800. In other words, when heat generated from the heaters 200 is released by using the heat sink 800, more power supplies and time may be necessary to heat the gas sensor. Accordingly, a heat loss may be minimized by releasing the heat of the gas sensor by using the heat sink 800 but confining the heat in the heat sink 800 by using the bottom cover 900.

Figure 8:
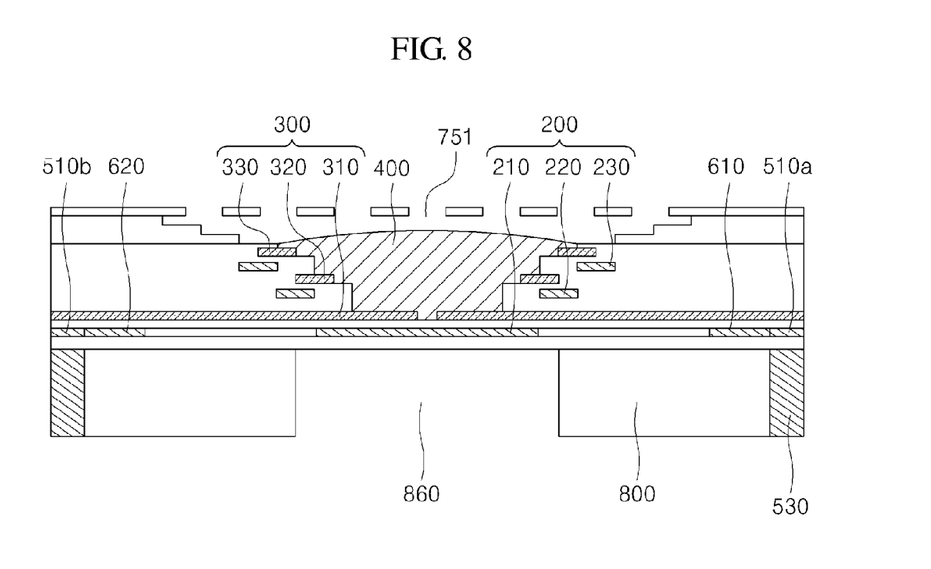
FIG. 8 is a combined cross-sectional view of a gas sensor in accordance with still another exemplary embodiment.

FIG. 8 is a combined cross-sectional view of a gas sensor in accordance with another exemplary embodiment.

Referring to FIG. 8, a gas sensor according an embodiment further includes a top cover 700 disposed on the top portion and a heat sink 800 disposed on the bottom portion. In other words, the gas sensor includes the plurality of insulating layers 100 (110 to 160), the heaters 200 formed on at least two selected insulating layers 100, the sensing electrodes 300 formed in at least two selected insulating layers 100 on which the heaters 200 are not formed, the sensing material 400 disposed in at least one insulating layer 100 to contact the sensing electrode 300, the top cover 700 formed on the insulating layer 160 to cover the sensing material 400, and the heat sink 800 disposed at the bottom portion of the insulating layer 110. In other words, the embodiment may be implemented by combining the embodiment described in relation to FIGS. 3 and 4, and the embodiment described in relation to FIGS. 5 and 6. The bottom cover 900 described in relation to FIG. 7 may be further disposed on the bottom portion of the heat sink 800. Accordingly, due to formation of the top cover 700, since a time taken for a gas flowed into the top cover 700 to contact the sensing material 400 becomes longer, reactivity and sensitivity can be improved. In addition, the formation of the heat sink 800 enables the heat generated from the gas sensor to be released.

Furthermore, in the embodiments, it is described a case where the heaters 200 and the sensing electrodes 300 respectively include three heat patterns 210, 220, and 230 and three sensing electrodes 310, 320, and 330. However, the heaters 200 and sensing electrodes 300 may respectively include at least two heater patterns and sensing electrode patterns. For example, six heater patterns stacked vertically and six sensing electrode patterns may be included. In addition, the number of heater patterns may be smaller than that of the sensing electrode patterns. For example, the heaters 200 may include only the heater pattern 210 formed on the first insulating layer 110 or one heater pattern may be disposed for every at least two sensing electrode patterns. In addition, for the sensing electrodes 300, a plurality of sensing electrode patterns are formed on different layers and the sensing electrode pattern formed on each layer may receive (+) and (−) powers. In other words, the sensing electrode patterns are respectively formed on four insulating layers, the sensing electrode pattern on every odd layer may receive (+) power and the sensing electrode pattern on every even layer may receive (−) power. In addition, the plurality of sensing electrode patterns 310, 320, and 330 may include at least one cut-out portion. In other words, like the first sensing electrode pattern 310, the electrodes may be separated to sense gases, and in the second and third sensing electrode patterns 320 and 330, at least one cut-out portion is formed to prepare at least two portions separated by a predetermined interval and accordingly a plurality of gas sensing areas may be disposed.

Figure 9:
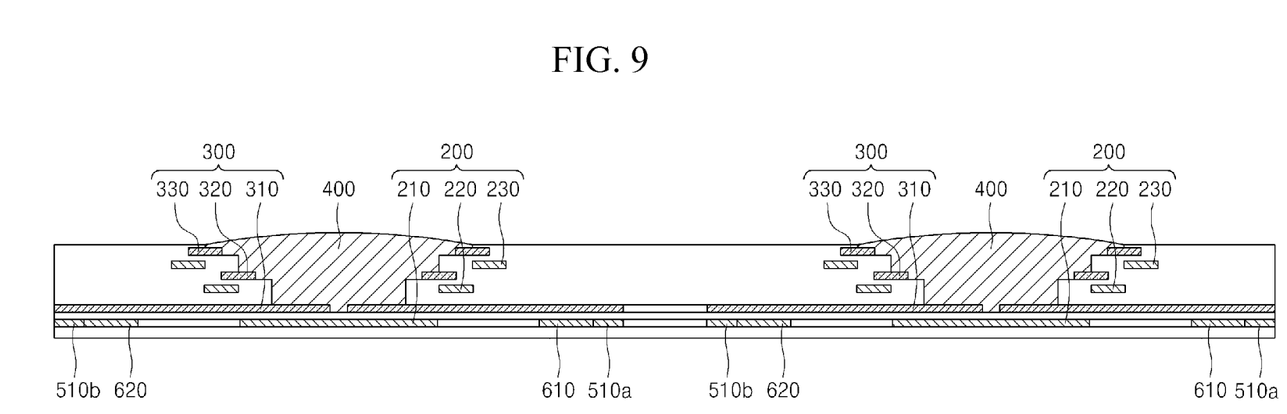
FIG. 9 is a combined cross-sectional view of a gas sensor in accordance with still another exemplary embodiment.

In addition, in the embodiments, a plurality of heaters 200 and sensing electrodes 300 are vertically separated, and the sensing material 400 is buried in the insulating layer 100 to implement one unit gas sensor. However, the gas sensor according to an embodiment may include such a unit gas sensor in plurality in a horizontal direction. In other words, a unit gas sensor in which the heaters 200, sensing electrodes 300 and the sensing material 400 are formed in a vertical direction may be arranged in plurality in the horizontal direction as illustrated in FIG. 9 to implement a gas sensor. At this point, the heaters 200 heating the plurality of unit gas sensors may be heated at different temperatures and the plurality of sensing materials 400 may also be formed of a plurality of different materials. Accordingly, a plurality of different gases may be sensed by using one gas sensor by disposing the plurality of unit gas sensors in a single package. At this point, the top cover, heat sink, and bottom cover described according to embodiments may also be applied to a gas sensor including the plurality of unit gas sensors.

Furthermore, for the gas sensor according to an embodiment illustrated in FIG. 9, since the plurality of heaters 200 heat at different temperatures, a predetermined time may be taken till the plurality of heaters 200 heat at set temperatures. In other words, a stabilization time may be necessary for the plurality of heaters 200 to be stabilized. For example, a predetermined time is necessary for the plurality of heaters 200 to be heated up to approximately 200° C., 300° C., 400° C., and 500° C., and as a heat temperature is higher, the stabilization time becomes longer. In other words, even though the first heater 210 is heated up to approximately 200° C. and stabilized, a time is further necessary till the fourth heater 240 is heated up to approximately 500° C. and stabilized. A base heater (not illustrated) may be further disposed to reduce a heating time of the plurality of heaters 200. The base heater may be disposed on the bottom side of the first insulating layer 110. In other words, when the base heater 800 is heated up to, for example, approximately 100° C., since the plurality of heaters 200 may be heated up to the set temperatures for example, approximately 100° C., 200° C., 300° C. and 400° C., the heating time may be reduced.

In a sensor according to embodiments, a heater in which a plurality of heater patterns are electrically connected in a vertical direction in a plurality of insulating layers and a sensing electrode in which a plurality of sensing electrode patterns are electrically connected are formed to be insulated from each other, and a sensing material is buried to contact the sensing electrode patterns in the plurality of insulating layers. Accordingly, a sensor having a 3-dimensional structure is implemented in which the heater and sensing electrode are formed in a vertical direction and the sensing material is buried therein. In addition, a top cover having a plurality of openings and meshes therein is formed on a top portion of the insulating layers can be further disposed and a heat sink can be further disposed on a bottom portion of the insulating layers.

According to an embodiment, the sensing material is buried in the insulating layer to prevent the sensing material from being desorbed and accordingly to improve shock-proof of a sensor.

In addition, the sensing material contacts the plurality of sensing electrode patterns to increase a contact area of the sensing material and the sensing electrode and to improve response and sensitivity of a sensor.

In addition, an exposed electrode is formed to be exposed externally on a plurality of flat insulating layers and the exposed electrode is soldered to enable a surface mount without wire bonding and mass production.

Furthermore, a heat sink can be further disposed to improve heat efficiency.

Although the sensor has been described with reference to the specific embodiments, it is not limited thereto. Therefore, it will be readily understood by those skilled in the art that various modifications and changes can be made thereto without departing from the spirit and scope of the present invention defined by the appended claims.

What is claimed is:
1. A sensor comprising:
an insulating layer;
at least two heater patterns separated in a vertical direction in the insulating layer and electrically connected to each other;

at least two sensing electrode patterns insulated from the heater patterns, separated in the vertical direction in the insulating layer, and electrically connected to each other; and a sensing material, at least a part of which is buried in the insulating layer to contact the sensing electrode patterns;

wherein the heater patterns and the sensing electrode patterns are alternately disposed in a vertical direction.

2. The sensor of claim 1, wherein the insulating layer comprises a plurality of stacked ceramic plates.

3. The sensor of claim 2, further comprising first and second exposed electrodes formed to be exposed externally at predetermined areas in the insulating layer and configured to supply power to each of the heaters and the sensing electrodes.

4. The sensor of claim 3, wherein the at least two heater patterns are respectively formed on top portions of at least two ceramic plates and connected through a hole with a conductive material buried therein.

5. The sensor of claim 4, wherein the at least two sensing electrode patterns are respectively formed on at least two ceramic plates and connected through a hole with a conductive material buried therein.

6. The sensor of claim 5, wherein the at least two sensing electrode patterns comprise a (+) power applied sensing electrode pattern and a (−) power applied sensing electrode pattern separated from each other.

7. The sensor of claim 5, wherein the sensing electrode patterns comprise at least one cut-out portion.

8. The sensor of claim 5, wherein the heat patterns and the sensing electrode patterns are formed on different ceramic plates to be alternately disposed in a stack direction of the ceramic plates.

9. The sensor of claim 8, wherein the sensing electrode patterns are formed to have diameters being wider progressively from a bottom side toward a top side.

10. The sensor of claim 9, wherein openings are formed inside the heater patterns and sensing electrode patterns in the at least two ceramic plates and buried with the conductive material.

11. The sensor of claim 10, wherein the openings are formed to expose the sensing electrode patterns thereunder.

12. The sensor of claim 1, further comprising a top cover disposed on a top portion of the insulating layer to cover the sensing material, wherein the top cover is formed of at least two stacked ceramic plates, or a metal or plastic, and comprising at least one opening or a mesh.

13. The sensor of claim 12, wherein the opening of the top cover is greater than that of the insulating layer.

14. The sensor of claim 12, further comprising a heat sink disposed on a bottom portion of the insulating layer, wherein the heat sink is formed of at least two stacked ceramic plates, and the at least one ceramic plate comprises an opening.

15. The sensor of claim 14, further comprising a third exposed electrode formed on a predetermined area of the heat sink, which corresponds to the first and second exposed electrodes.

16. The sensor of claim 14, further comprising a bottom cover disposed on a bottom portion of the heat sink.

17. A sensor comprising:

a plurality of unit sensors each comprising heaters, sensing electrodes, and a sensing material formed in a vertical direction in an insulating layer to sense at least one gas;

wherein the heaters, the sensing electrodes, and the sensing material are disposed in plurality in a horizontal direction and sense a plurality of different subjects;

wherein the heaters are separated in the vertical direction in the insulating layer and electrically connected to each other;

wherein the sensing electrodes are insulated from the heaters and vertically separated in the insulating layer to be electrically connected to each other;

wherein at least a part of the sensing material is buried in the insulating layer to contact the sensing electrodes; and wherein the plurality of heaters arranged in the horizontal direction heat at at least two temperatures.

18. The sensor of claim 17, wherein the plurality of sensing electrodes respectively comprise at least one cut-out portion.

19. The sensor claim 18, wherein the plurality of sensing materials are formed of at least two materials.

20. The sensor of claim 17, further comprising:

a top cover disposed on a top portion of the insulating layer to cover the sensing material;

a heat sink disposed on a bottom portion of the insulating layer; and a bottom cover disposed on a bottom portion of the heat sink.

21. A sensor comprising:

an insulating layer;

at least two heater patterns separated in a vertical direction in the insulating layer and electrically connected to each other;

at least two sensing electrode patterns insulated from the heater patterns, separated in the vertical direction in the insulating layer, and electrically connected to each other; and a sensing material, at least a part of which is buried in the insulating layer to contact the sensing electrode patterns;

wherein the heater patterns and the sensing electrode patterns are alternately disposed in a vertical direction; and wherein the heaters, the sensing electrodes, and the sensing material are disposed in plurality in a horizontal direction and sense a plurality of different subjects.

* * * * *